US012168070B2

(12) United States Patent
Rutolo, Jr. et al.

(10) Patent No.: US 12,168,070 B2
(45) Date of Patent: *Dec. 17, 2024

(54) TRANSMUCOSAL AND TRANSDERMAL DELIVERY SYSTEMS

(71) Applicant: Medlab Clinical U.S., Inc., Rancho Santa Margarita, CA (US)

(72) Inventors: David A. Rutolo, Jr., Rancho Santa Margarita, CA (US); Sean Michael Hall, Millers Point (AU); Luis Vitetta, Varsity Lakes (AU); Yusi Zhou, Hornsby (AU); Samantha Maree Coulson, Fig Tree Pocket (AU)

(73) Assignee: Medlab Clinical U.S., Inc., Rancho Santa Margarita, CA (US)

( * ) Notice: Subject to any disclaimer, the term of this patent is extended or adjusted under 35 U.S.C. 154(b) by 524 days.

This patent is subject to a terminal disclaimer.

(21) Appl. No.: 17/492,386

(22) Filed: Oct. 1, 2021

(65) Prior Publication Data

US 2022/0023199 A1 Jan. 27, 2022

Related U.S. Application Data

(63) Continuation of application No. 15/555,038, filed as application No. PCT/US2016/020468 on Mar. 2, 2016, now Pat. No. 11,160,753.

(Continued)

(51) Int. Cl.
| | |
|---|---|
| *A61K 9/00* | (2006.01) |
| *A61K 9/08* | (2006.01) |
| *A61K 9/107* | (2006.01) |
| *A61K 9/70* | (2006.01) |
| *A61K 31/05* | (2006.01) |
| *A61K 31/07* | (2006.01) |
| *A61K 31/122* | (2006.01) |
| *A61K 31/135* | (2006.01) |
| *A61K 31/197* | (2006.01) |
| *A61K 31/355* | (2006.01) |
| *A61K 31/375* | (2006.01) |
| *A61K 31/40* | (2006.01) |
| *A61K 31/4045* | (2006.01) |
| *A61K 31/4188* | (2006.01) |
| *A61K 31/43* | (2006.01) |
| *A61K 31/4415* | (2006.01) |
| *A61K 31/505* | (2006.01) |
| *A61K 31/51* | (2006.01) |
| *A61K 31/525* | (2006.01) |
| *A61K 31/565* | (2006.01) |
| *A61K 31/568* | (2006.01) |
| *A61K 31/57* | (2006.01) |
| *A61K 31/573* | (2006.01) |

(Continued)

(52) U.S. Cl.
CPC ............ *A61K 9/006* (2013.01); *A61K 9/0014* (2013.01); *A61K 9/0043* (2013.01); *A61K 9/08* (2013.01); *A61K 9/107* (2013.01); *A61K 9/7015* (2013.01); *A61K 31/05* (2013.01); *A61K 31/07* (2013.01); *A61K 31/122* (2013.01); *A61K 31/135* (2013.01); *A61K 31/197* (2013.01); *A61K 31/355* (2013.01); *A61K 31/375* (2013.01); *A61K 31/40* (2013.01); *A61K 31/4045* (2013.01); *A61K 31/4188* (2013.01); *A61K 31/43* (2013.01); *A61K 31/4415* (2013.01); *A61K 31/505* (2013.01); *A61K 31/51* (2013.01); *A61K 31/525* (2013.01); *A61K 31/565* (2013.01); *A61K 31/568* (2013.01); *A61K 31/57* (2013.01); *A61K 31/573* (2013.01); *A61K 31/592* (2013.01); *A61K 31/593* (2013.01); *A61K 31/675* (2013.01); *A61K 31/714* (2013.01); *A61K 33/00* (2013.01); *A61K 33/06* (2013.01); *A61K 33/26* (2013.01); *A61K 33/30* (2013.01); *A61K 33/32* (2013.01); *A61K 33/34* (2013.01); *A61K 33/42* (2013.01); *A61K 36/185* (2013.01); *A61K 38/05* (2013.01); *A61K 38/28* (2013.01); *A61K 47/10* (2013.01); *A61K 47/12* (2013.01); *A61K 47/14* (2013.01); *A61K 47/44* (2013.01)

(58) Field of Classification Search
CPC .... A61K 9/0014; A61K 9/0043; A61K 9/006; A61K 9/08; A61K 9/107
See application file for complete search history.

(56) References Cited

U.S. PATENT DOCUMENTS

| 5,338,538 A | 8/1994 | Tricca et al. |
| 6,294,192 B1 | 9/2001 | Patel et al. |

(Continued)

FOREIGN PATENT DOCUMENTS

| CN | 101032452 A | 9/2007 |
| EP | 0 509 761 A1 | 10/1992 |

(Continued)

OTHER PUBLICATIONS

Ma "Cholesterol and Human Health", Nature and Science, 2(4), 2004, Supplement, Ma, Cholesterol and Human Health (Year: 2004).*

(Continued)

*Primary Examiner* — Ruth A Davis
(74) *Attorney, Agent, or Firm* — Seed IP Law Group LLP

(57) ABSTRACT

Provided herein are transmucosal and transdermal delivery systems comprising: at least one non-ionic surfactant; at least one polyol; and at least one active agent; and optionally further comprising at least one oil. In particular embodiments, the delivery system has an average particle size of from about 5 nm to about 200 nm.

19 Claims, No Drawings

Related U.S. Application Data

(60) Provisional application No. 62/127,200, filed on Mar. 2, 2015, provisional application No. 62/199,007, filed on Jul. 30, 2015.

(51) Int. Cl.

| | | |
|---|---|---|
| A61K 31/592 | (2006.01) | |
| A61K 31/593 | (2006.01) | |
| A61K 31/675 | (2006.01) | |
| A61K 31/714 | (2006.01) | |
| A61K 33/00 | (2006.01) | |
| A61K 33/06 | (2006.01) | |
| A61K 33/26 | (2006.01) | |
| A61K 33/30 | (2006.01) | |
| A61K 33/32 | (2006.01) | |
| A61K 33/34 | (2006.01) | |
| A61K 33/42 | (2006.01) | |
| A61K 36/185 | (2006.01) | |
| A61K 38/05 | (2006.01) | |
| A61K 38/28 | (2006.01) | |
| A61K 47/10 | (2017.01) | |
| A61K 47/12 | (2006.01) | |
| A61K 47/14 | (2017.01) | |
| A61K 47/44 | (2017.01) | |

(56) References Cited

U.S. PATENT DOCUMENTS

| | | | |
|---|---|---|---|
| 8,858,962 | B2 | 10/2014 | Tokumoto et al. |
| 11,160,753 | B2 * | 11/2021 | Rutolo, Jr. ............. A61K 31/05 |
| 2003/0170295 | A1 | 9/2003 | Kim et al. |
| 2004/0120994 | A1 | 6/2004 | Theobald |
| 2005/0197501 | A1 | 9/2005 | Niddam-Hildesheim et al. |
| 2007/0243132 | A1 | 10/2007 | Russell-Jones et al. |
| 2008/0014166 | A1 | 1/2008 | Klug et al. |
| 2008/0138296 | A1 | 6/2008 | Tamarkin et al. |
| 2009/0075860 | A1 | 3/2009 | Yamaguchi et al. |
| 2011/0318405 | A1 | 12/2011 | Erwin |
| 2012/0071390 | A1 | 3/2012 | Fenyvesi et al. |
| 2012/0289589 | A1 | 11/2012 | Travis |
| 2012/0328549 | A1 | 12/2012 | Edelson et al. |
| 2013/0064825 | A1 | 3/2013 | Chan et al. |
| 2014/0010882 | A1 | 1/2014 | Matsuda et al. |

FOREIGN PATENT DOCUMENTS

| | | |
|---|---|---|
| EP | 0 812 587 A1 | 12/1997 |
| WO | 99/00135 A1 | 1/1999 |
| WO | 00/50007 A1 | 8/2000 |
| WO | 2011/086093 A2 | 7/2011 |
| WO | 2011/121496 A1 | 10/2011 |
| WO | 2013/088161 A1 | 6/2013 |
| WO | 2014/036954 A1 | 3/2014 |

OTHER PUBLICATIONS

Aungst et al. "Comparison of the effects of various transmucosal absorption promoters on buccal insulin delivery," *International Journal of Pharmaceutics* 53:227-235, 1989.

Cormack Packaging, "MK VII Fine Mist Sprayer (/products/fine-mist-sprayers/item/mk-vi-fine-mist-sprayer-24-410," URL: www.cormack.com.au/products/fine-mist-sprayers/item/mk-vi-fine-mist-sprayer-24-410, Dec. 4, 2019, 3 pages.

E.D. Luce Packaging, "Spray Misters, Fine Mist Spray Misters," URL: www.//essentialsupplies.com/spray-misters.html, 2019, 3 pages.

El-Leithy et al., "In vitro and in vivo evaluation of indomethacin nanoemulsion as a transdermal delivery system," *Drug Delivery* 22(8):1010-1017, 2015. (9 Pages).

Luo et al., "Study on a Nanoparticle System for Buccal Delivery of Insulin," *27th IEEE Annual Conference on Engineering in Medicine and Biology*, Shanghai, China, Sep. 1-4, 2005, pp. 4842-4845.

Wang et al., "Effects of surfactant micelles on viscosity and conductivity of poly(ethylene glycol) solutions," *J. Chem. Phys.* 120:4980, 10 pages, 2004.

Zhao et al., "Nonionic Surfactant and Temperature Effects on the Viscosity of Hydrophobically Modified Hydroxyethyl Cellulose Solutions," *J. Phys. Chem.* 109:14198-14204, 2005.

* cited by examiner

1

TRANSMUCOSAL AND TRANSDERMAL DELIVERY SYSTEMS

FIELD OF THE ART

The present invention relates generally to transmucosal (typically oral and/or nasal) and transdermal delivery systems and methods for making such delivery systems.

BACKGROUND

Oral formulations for the delivery of vitamins, minerals and active pharmaceutical ingredients include tablets, capsules (hard and soft shelled), lozenges, powders, emulsions and liquids. In order to benefit from such formulations and ensure optimum absorption of the vitamins, minerals or active pharmaceutical ingredients the subject must have a well functioning gastrointestinal system that ensures adequate absorption via the gastrointestinal tract. Not all subjects have a well functioning gastrointestinal system and therefore can not make use of such oral formulations. It is therefore beneficial to produce formulations that can be absorbed transdermally or via the oral and/or nasal mucosa, for example via the highly vascularized oral-buccal mucosa, such that the vitamins, minerals or active pharmaceutical ingredients are provided direct access to the body's systemic circulation system via capillaries thereby bypassing the gastrointestinal tract.

Many active pharmaceutical ingredients, for example insulin, are typically administered via needle and syringe, and the like such as pens, jet injectors and pumps. Many people find such administration devices to be daunting, uncomfortable and generally inconvenient. It is therefore beneficial to produce formulations that can be absorbed via the oral and/or nasal mucosa, for example via the highly vascularized buccal/sublingual mucosa, such that the insulin is provided direct access to the body's systemic circulation system via capillaries thereby avoiding the need to break the skin.

The present inventors have found that transdermal and transmucosal (oral and/or nasal) delivery systems comprising at least one non-ionic surfactant; at least one polyol; and at least one active agent can be successfully administered bypassing the gastrointestinal tract and avoiding the need to break the skin.

SUMMARY OF THE DISCLOSURE

A first aspect of the invention provides a transmucosal and/or transdermal delivery system comprising at least one non-ionic surfactant; at least one polyol; and at least one active agent. The transmucosal delivery may be via the oral mucosa and/or the nasal muscosa.

In certain embodiments the delivery system further comprises at least one oil. The at least one oil may be ethyl oleate, ethyl linoleate, caproic acid, caprylic acid, capric acid, or lauric acid, or a combination thereof. In particular embodiments the at least one oil is a natural oil or is derived from a natural oil. Typically the natural oil is coconut oil, palm kernel oil, palm oil, lemon oil, or sunflower oil, or a combination thereof.

Typically the at least one non-ionic surfactant is selected from the group consisting of a polyethoxylated castor oil, polyoxyethylene sorbitan monolaurate, polyoxyethylene sorbitan monoleate and tocopheryl polyethylene glycol succinate. In one embodiment the at least one non-ionic surfactant is a polyethoxylated castor oil. The at least one non-ionic surfactant may be obtained by reacting castor oil or hydrogenated castor oil with ethylene oxide. In one embodiment the at least one non-ionic surfactant is a polyethoxylated castor oil. In another embodiment the at least one non-ionic surfactant comprises glycerol polyethylene glycol ricinoleate, fatty acid esters of polyethylene glycol, free polyethylene glycols and ethoxylated glycerol. In another embodiment the at least one non-ionic surfactant comprises glycerol polyethylene glycol hydroxystearate, fatty acid glycerol polyglycol esters, polyethylene glycols and glycerol ethoxylate.

Typically the at least one polyol is selected from the group consisting of glycerol and propylene glycol. In one embodiment the at least one polyol is glycerol. In another embodiment the at least one polyol is propylene glycol.

Typically the active agent is a pharmaceutically active ingredient. In exemplary embodiments the at least one active agent is selected from the group consisting of a vitamin, a mineral, a hormone, an amino acid, a peptide, a fatty acid, an antioxidant, a plant extract, a nutraceutical, a statin, an immunosuppressive agent, an antibiotic, a sedative, a steroid, a proton pump inhibitor (PPI), a selective serotonin reuptake inhibitor (SSRI), an angiotensin converting enzyme (ACE) inhibitor and combinations thereof.

In particular embodiments the active agent is a statin. The stain may be fat soluble or water soluble. In one embodiment the fat soluble statin is atorvastatin. In an exemplary embodiment the atorvastatin is atorvastatin calcium. In some embodiments the fat soluble statin is provided in oil or an oil mixture. In certain embodiments the at least one fat soluble statin is provided in ethanol or an ethanol and oil solution. In particular embodiments the statin is a water soluble statin. In one embodiment the water soluble statin is rosuvastatin. In an exemplary embodiment the atorvastatin is rosuvastatin calcium.

In some embodiments the at least one active agent is a vitamin. Typically, the vitamin is selected from the group consisting of vitamin A, vitamin B, vitamin C, vitamin D, vitamin E and vitamin K. In particular embodiments the vitamin is selected from the group consisting of vitamin B1, vitamin B2, vitamin B5, vitamin B6, vitamin B7, vitamin B9 and vitamin B12. In one embodiment the vitamin is vitamin B12. The vitamin B12 may be methylcobalamin and/or cyanocobalamin. In another embodiment the vitamin is B6. The vitamin B6 may be pyridoxine hydrochloride. In particular embodiments the vitamin is D2 or vitamin D3. In one embodiment the vitamin D3 is cholecalciferol. In particular embodiments the vitamin is vitamin E. In one embodiment the vitamin E is d-alpha-tocopherol. In particular embodiments the vitamin is vitamin K2. In one embodiment the vitamin K2 is menaquinone-4 or menaquinone-7. In one embodiment the vitamin is a combination of vitamin D3 and vitamin K2.

In some embodiments the at least one active agent is an antioxidant. The antioxidant may be Coenzyme Q10.

In some embodiments the at least one active agent is a plant extract. The plant extract may be a natural extract or a synthetic version thereof. The plant extract may be resveratrol, cannabis, or hemp oil.

In some embodiments the at least one active agent is a mineral. Typically, the mineral is selected from the group consisting of zinc, calcium, chromium, cooper, iron, magnesium, manganese, phosphorus, potassium. In one embodiment the mineral is zinc.

In some embodiments the at least one active agent is a hormone. The hormone may be selected from the group consisting of melatonin, insulin, testosterone, progesterone and estrogen. The testosterone may be testosterone propionate. In an exemplary embodiment the hormone may be insulin. In another exemplary embodiment the hormone may be progestogen. In yet another exemplary embodiment the hormone may be beta-estradiol.

In another embodiment, the delivery system further comprises water. Typically, the ratio of water to the at least one active agent, at least one non-ionic surfactant and at least one polyol is from about 3:1 to about 2:1 by weight.

In another embodiment the delivery system further comprises a non-aqueous solvent or a mixture of a non-aqueous solvent and water. In certain embodiments the delivery system comprises ethanol and/or water.

In another embodiment, the delivery system further comprises at least one flavour. The at least one flavour may be a natural oil. The natural oil is typically peppermint oil or orange oil.

In another embodiment, the delivery system further comprises at least one acidulant. The at least one acidulant may be citric acid.

In another embodiment, the delivery system further comprises at least one preservative. The at least one preservative may be potassium sorbate or phenoxyethanol.

In another embodiment, the delivery system further comprises at least one sweetener. The at least one sweetener may be a natural sweetener. In one embodiment the natural sweetener is stevia.

In one embodiment the at least one non-ionic surfactant has an Hydrophile-Lipophile Balance (HLB) value of from about 8 to about 20. In particular embodiments the at least one non-ionic surfactant has an Hydrophile-Lipophile Balance (HLB) value of from about 12 to about 16.

The viscosity of the delivery system may be about 5 cP to about 35 cP. In one embodiment the viscosity of the delivery system is from about 10 cP to about 20 cP.

The average size of particles in the delivery system may be up to about 300 nm. In one embodiment the average particle size is from about 1 nm to about 200 nm. In another embodiment the average particle size is from about 5 nm to about 100 nm.

In one embodiment the ratio of the at least one active agent to the at least one non-ionic surfactant may be from about 1:5 to about 1:15 by weight. In one embodiment the ratio of the at least one non-ionic surfactant to the at least one polyol is from about 2:1 to about 1.5:1 by weight.

Also provided are oral and/or nasal transmucosal delivery systems and transdermal delivery systems comprising: at least one non-ionic surfactant; at least one polyol; and at least one active agent, wherein the at least one non-ionic surfactant has an Hydrophile-Lipophile Balance (HLB) value of from about 12 to about 16; the delivery system has a viscosity of from about 5 cP to about 35 cP; the delivery system has an average particle size of about 200 nm; the ratio of the at least one active agent to the at least one non-ionic surfactant is from about 1:5 to about 1:15 by weight; and the ratio of the at least one non-ionic surfactant to the at least one polyol is from about 2:1 to about 1.5:1 by weight. In a particular embodiment the viscosity of the delivery system is from about 10 cP to about 20 and/or the particle size of the delivery system is from about from about 1 nm to about 200 nm.

A second aspect of the invention provides a method for preventing and/or reducing blood cholesterol in a subject, the method comprising administering an effective amount of the delivery system the first aspect to the subject, wherein the active agent in the delivery system is a statin.

A third aspect of the invention provides a method for treating dyslipidemia in a subject, the method comprising administering an effective amount of the delivery system of the first aspect to the subject, wherein the active agent in the delivery system is a statin.

A method for preventing and/or treating cardiovascular disease in a subject, the method comprising administering an effective amount of the delivery system of any one of the first aspect the subject, wherein the active agent in the delivery system is a statin.

A method for treating diabetes, for regulating blood glucose levels and/or for preventing or treating hyperglycaemia in a subject, the method comprising administering an effective amount of the first aspect to the subject, wherein the active agent in the delivery system is insulin.

DETAILED DESCRIPTION

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

Throughout this specification and the claims which follow, unless the context requires otherwise, the word "comprise", and variations such as "comprises" or "comprising", will be understood to imply the inclusion of a stated element, integer or step, or group of elements, integers or steps, but not the exclusion of any other element, integer or step, or group of elements, integers or steps.

The articles "a" and "an" are used herein to refer to one or to more than one (i.e., to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

The term "subject" as used herein refers to any mammal, including, but not limited to, livestock and other farm animals (such as cattle, goats, sheep, horses, pigs and chickens), performance animals (such as racehorses), companion animals (such as cats and dogs), laboratory test animals and humans. Typically the subject is a human.

As used herein the terms "treating", "treatment", "treating", "reduce", "reducing", "prevent" "preventing" and "prevention" and the like refer to any and all applications which remedy, or otherwise hinder, retard, or reverse the progression of, an infection or disease or at least one symptom of an infection or disease, including reducing the severity of an infection or disease. Thus, the terms "treat", "treating", "treatment", do not necessarily imply that a subject is treated until complete elimination of the infection or recovery from a disease. Similarly, the terms "prevent", "preventing", "prevention" and the like refer to any and all applications that prevent the establishment of an infection or disease or otherwise delay the onset of an infection or disease.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

As used herein the terms "effective amount" and "effective dose" include within their meaning a non-toxic but sufficient amount or dose of a fat soluble statin to provide the desired effect. The exact amount or dose required will vary from subject to subject depending on factors such as the species being treated, the age and general condition of the subject, the severity of the condition being treated, the particular statin being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

As used herein the term "delivery system" refers to a composition comprising a formulation according to the invention which is particularly adapted for delivery of active agents transdermally or via the oral and/or nasal mucosa. Typically the particle size of the delivery system is from about 1 to about 200 nm.

As used herein, the term "oral" refers to a delivery system that can be administered orally. The term "oral" includes ingestion and oral transmucosal delivery, for example, buccal and/or sublingual delivery.

As used here, the term "transdermal" refers to a delivery system that can be administered to the skin, wherein the active agent is delivered across the skin for systemic distribution.

As used herein the term "extract" refers to an active preparation derived from one or more plants or a synthetic version thereof. In the context of the specification by "active" it is meant that the extract is capable of producing a desired therapeutic benefit. An extract is obtained by a process of "extraction" which will be understood by those skilled in the art as, in general terms, comprising treating plant material with a solvent, a liquid, or a supercritical fluid to dissolve the active preparation and separate the same from residual unwanted plant material. An extract may be in liquid form (for example as a decoction, solution, infusion or tincture) or solid form (for example as a powder or granules). An extract may comprise a single active agent or a combination of active agents.

As used herein the term "oil" refers to a nonpolar chemical substance that is hydrophobic and lipophilic. Those skilled in the art will appreciate that an oil may be a natural oil that it is animal, plant or petrochemical in origin; may be derived from or extracted from a natural oil via a physical or chemical process; or may be a synthetic oil. Oils such as fatty acids or fatty acid esters may be derived from or extracted from a natural oil or prepared synthetically. For example, caprylic acid is a fatty acid found in naturally in milk fat, coconut oil and palm kernel oil and can also be made synthetically.

In the context of this specification, the term "plant" refers to any living organism that grows in the earth, including but not limited to, trees, shrubs, flowers, bushes, herbs, grasses, ferns, and mosses and any plant material derived therefrom (for example, fruit, fruit skin, leaves, seed, bark, roots, stems and the like).

The present inventor has developed, a composition specifically adapted for delivery of nutritionally and pharmaceutically beneficial agents transdermally or via the oral and/or nasal mucosa. Embodiments of the present invention provide an oral and/or nasal transmucosal delivery system or a transdermal delivery system comprising at least one non-ionic surfactant; at least one polyol; and at least one active agent. In some embodiments the delivery system further comprises at least one oil. The present invention beneficially provides delivery of an active agent via the oral and/or nasal transmucosal or transdermal route, thereby bypassing the gastrointestinal tract and avoiding the need to break the skin, as with, for example an injection, and ensuring rapid absorption by the bloodstream. Whilst being advantageous of the administration of active agents to any individual, delivery systems of the invention will find particular use in subjects with an impaired or non-functioning gastrointestinal system that cannot effectively absorb active agents via the gastrointestinal tract. The delivery systems also benefit those subjects who are unable to swallow oral dosage forms. The delivery systems also benefit those who cannot tolerate injections or find injections daunting, uncomfortable and generally inconvenient.

Transmucosal delivery systems according to the invention may be in any form suitable for delivery of active agents via the oral and/or nasal mucosa, including for example, but not limited to, sprays, pumps, gels including mucoadhesive polymeric gels, foams and quick dissolve tablets. The skilled artisan will appreciate that the transmucosal delivery systems are not so limited and that any transmucosal formulations may be employed.

Transdermal delivery systems according to the invention may be in any form suitable for delivery of active agents transdermally, including for example, but not limited to, sprays, lotions, gels, creams, patches and implants. The transdermal delivery systems may employ chemical enhancers which aid dermal penetration and/or use ultrasound or iontophoresis for the improved delivery of drug molecules that do not easily undergo passive diffusion. Microneedles and electroporation type transdermal delivery forms may also be used with the delivery systems according to the invention. The skilled artisan will appreciate that the transdermal delivery systems are not so limited and that any transdermal formulations may be employed.

In particular embodiments the formulation of the delivery system is such that it provides a fine micellized mist spray comprising the active agent, the spray being suitable for administration orally, for buccal or other oral mucosal delivery, intranasally for delivery via the nasal mucosa, or transdermally across the skin. Without wishing to be bound by theory, the fine mist ensures maximum surface coverage and therefore optimum delivery of the active agent(s) via the oral and/or nasal mucosa. In some embodiments the Hydrophile-Lipophile Balance (HLB) of the non-ionic surfactant, the particular ratio of the at least one active agent to the at least one non-ionic surfactant, and the ratio of the at least one non-ionic surfactant to the at least one polyol assist to provide a delivery system with the necessary characteristics such as small particle size and viscosity, to produce a formulation adapted for oral and/or nasal transmucosal delivery.

While a fine mist spray for oral delivery via the buccal mucosa, intranasal delivery via the nasal mucosa, or transdermal delivery across the skin is one particularly advantageous form of the delivery system, those skilled in the art will appreciate that the delivery system may be delivered in a form other than a spray. Sprays and other forms of the delivery systems of the invention may be administered using any suitable conventional administration means. For example a spray delivery system of the invention may be administered via a pump action or pressurized administration vessel such as an aerosol spray. In particular embodiments the administration means may provide metered doses of the composition. In some embodiments the delivery systems are absorbed onto solid carriers such as, but not limited to, powders, granules, or beads. The powders may include but are not limited to lyophilised bacteria.

In accordance with embodiments of the invention, the delivery systems may be administered transdermally to any external skin of a subject. The skin area may be, for example, the scalp, hands, arms, underarms, face, groin or feet. Those skilled in the art will readily appreciate however that any surface, organic or inorganic in nature, may be the subject of treatment in accordance with embodiments of the invention. Transdermal delivery systems compositions according to the invention may further comprise preservative(s), moisturizer(s), carrier(s), excipient(s), diluent(s) and/or adjuvant(s). In a particular embodiment the transdermal delivery system comprises phenoxyethanol as a preservative and allantoin as a moisturizer. In particular embodiments the pH of the transdermal delivery system may be adjusted to about pH 4 to about pH 8. Typically, the pH of the transdermal delivery system is from about pH 5.0 to pH 6.0. For example, the pH of the transdermal delivery system may be about pH 5.1, pH 5.2, pH 5.3, pH 5.4, pH 5.5, pH 5.6, pH, 5.7, pH 5.8, or pH 5.9.

Transdermal delivery systems of the invention may also include compounds which enhance dermal penetration, such as, for example, anionic surfactants, cationic surfactants, zwitterionic surfactants, nonionic surfactants, fatty acids, fatty esters, fatty amines, terpenes, sulphoxides, laurocapram, pyrrolidones, alcohol, glycol, urea and skin penetration enhancing peptides.

The delivery systems of the invention may further comprise at least one oil. In some embodiments the at least one active agent may be provided in the oil or in an oil/solvent mixture. In particular embodiments the at least one active agent may be a fat soluble statin such such as but not limited to atorvastatin; a fat soluble vitamin, such as but not limited to, vitamin K2 (for example, menaquinone 7), a fat soluble hormone, such as but not limited to testosterone and/or a fat soluble pharmaceutical agent. The oil or oil mixture may act as a carrier or solvent for the at least one active agent. The oil or oil mixture may increase the stability of the stability system. The oil may be a natural oil in that it is animal, plant or petrochemical in origin; may be derived from or extracted from a natural oil via a physical or chemical process; or may be synthetic oil. Examples of suitable oils include, but are not limited to lemon oil, sunflower oil, soybean oil, canola oil, olive oil, corn oil, peanut oil, groundnut oil, rice bran oil, coconut oil, cottonseed oil, flax seed oil, palm oil, palm kernel oil, safflower oil, soybean oil, sesame oil, amaranth oil, linseed oil, argan oil, grapeseed oil, cranberry seed oil. hazelnut oil. hemp oil, jojoba oil, macadamia oil, mustard oil, neem oil, orange oil, rapeseed oil, avocado oil, almond oil, sweet almond oil, cashew oil, castor oil, vegetable oil, walnut oil, wheatgerm oil, kukui nut oil, tamuna oil, aloe vera oil, apricot kernel oil, borage oil (from, for example *Borago officinalis*), *camellia* oil (from, for example, *Camellia oleifera*), cocoa butter oil, rosehip see oil, fish oils, ethyl oleate, ethyl linoleate, saturated fatty acids (such as, but not limited to, caproic acid, caprylic acid, capric acid, lauric acid, valeric acid, myristic acid, palmitic acid, stearic acid, arachidic acid), medium chain triglycerides, omega-3 fatty acids (such as, but not limited to, hexadecatrienoic acid, alpha-linolenic acid, stearidonic acid, ecosatrienoic acid, eicosapentaenoic acid, heneicosapentanoic acid, docosapentanoic acid, docosahexanoic acid, tetracosapentaenoic acid, tetracosahexanenoic acid), omega-6 fatty acids (such as, but not limited to, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid), and/or omega-9 fatty acids (such as, but not limited to, oleic acid, eicosenoic acid, mead acid, erucic acid, nervonic acid). In particular embodiments the oil is olive oil, medium chain triglycerides, ethyl oleate, ethyl linoleate, caproic acid, caprylic acid, capric acid, or lauric acid, or a combination thereof. The oil mixture may comprise an oil, a non-aqueous solvent (such as an organic solvent or an inorganic solvent and/or mixtures thereof) and/or water. The oil may be a natural oil in that it is animal, plant or petrochemical in origin; may be derived from or extracted from a natural oil via a physical or chemical process; or may be synthetic oil. Suitable organic solvents are known to those skilled in the art and may include, but are not limited to polar solvents (for example ethanol), non-polar solvents (for example hexane) and/or halogenated solvents (for example dichloromethane).

The ratio of oil and at least one active agent to at least one non-ionic surfactant may be from about 1:2 to about 1:8 by weight. Typically, the ratio of water to the at least one active agent, at least one non-ionic surfactant and at least one polyol is from about 1:4.5 to about 1:6.5 by weight. For example, the ratio of oil and at least one active agent to at least one non-ionic surfactant may be about 1:4.6 by weight, 1:4.7 by weight, 1:4.8 by weight, 1:4.9 by weight, 1:5.0 by weight, 1:5.1 by weight, 1:5.2 by weight, 1:5.3 by weight, 1:5.4 by weight, 1:5.5 by weight, 1:5.6 by weight, 1:5.7 by weight, 1:5.8 by weight, 1:5.9 by weight, 1:6.0 by weight, 1:6.1 by weight, 1:6.2 by weight, 1:6.3 by weight, or 1:6.4 by weight.

In some embodiments the non-ionic surfactant may have an Hydrophile-Lipophile Balance (HLB) value of from about 8 to about 20. In accordance with particular embodiments of the invention the non-ionic surfactant may have an Hydrophile-Lipophile Balance (HLB) value of from 10 to 18, or more typically of from 11 to 17. For example, the non-ionic surfactant may have an Hydrophile-Lipophile Balance (HLB) value of 11, 12, 13, 14, 15, 16 or 17.

In some embodiments the viscosity of the delivery system may be about 5 cP to about 35 cP. In accordance with particular embodiments of the invention the viscosity of the delivery system is from about 8 cP to about 30 cP. For example, the viscosity of the delivery system may be about 8 cP, 9 cP, 10 cP, 11 cP, 12 cP, 13 cP, 14 cP, 15 cP, 16 cP, 17 cP, 18 cP, 19 cP, 20 cP, 21 cP, 22 cP, 23 cP, 24 cP, 25 cP, 26 cP, 27 cP, 28 cP, 29 cP or 30 cP.

In some embodiments the average size of particles in the delivery system may be up to about 300 nm. In accordance with particular embodiments of the invention the average particle is from about 1 nm to about 250 nm. In accordance with particular embodiments of the invention the average particle size is about 5 nm, 10 nm, 15 nm, 20 nm, 25 nm, 30 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, or 200 nm. In accordance with particular embodiments of the invention the average particle size is from about 1 nm to about 100 nm. For example, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm 94 nm, 95 nm, 96 nm, 97 nm, 98 nm, 99 nm or 100 nm.

In some embodiments the ratio of the at least one active agent to the at least one non-ionic surfactant may be from about 1:5 to about 1:15 by weight. For example, the ratio of the at least one active agent to the at least one non-ionic surfactant may be about 1:5 by weight, 1:5.5 by weight, 1:6 by weight, 1:6.5 by weight, 1:7 by weight, 1:7.5 by weight, 1:8 by weight, 1:8.5 by weight, 1:9 by weight, 1:9.5 by weight, 1:10 by weight, 1:10.5 by weight, 1:11 by weight, 1:11.5 by weight, 1:12 by weight, 1:12.5 by weight, 1:13 by weight, 1:13.5 by weight, 1:14 by weight, 1:14.5 by weight or 1:15 by weight.

In some embodiments the ratio of the at least one non-ionic surfactant to the at least one polyol may be from about 2:1 to about 1.5:1 by weight. For example, the ratio of the at least one non-ionic surfactant to the at least one polyol may be about 2:1 by weight, 1.99:1 by weight, 1.98:1 by weight, 1.97 by weight, 1.96 by weight, 1.95:1 by weight, 1.94:1 by weight, 1.93:1 by weight, 1.92:1 by weight, 1.91:1 by weight, 1.90:1 by weight, 1.89:1 by weight, 1.88:1 by weight, 1.87 by weight, 1.86 by weight, 1.85:1 by weight, 1.84:1 by weight, 1.83:1 by weight, 1.82:1 by weight, 1.81:1 by weight, 1.80:1 by weight, 1.79:1 by weight, 1.78:1 by weight, 1.77 by weight, 1.76 by weight, 1.75:1 by weight, 1.74:1 by weight, 1.73:1 by weight, 1.72:1 by weight, 1.71:1 by weight, 1.70:1 by weight, 1.69:1 by weight, 1.68:1 by weight, 1.67 by weight, 1.66 by weight, 1.65:1 by weight, 1.64:1 by weight, 1.63:1 by weight, 1.62:1 by weight, 1.61:1 by weight, 1.60:1 by weight, 1.59:1 by weight, 1.58:1 by weight, 1.57 by weight, 1.56 by weight, 1.55:1 by weight, 1.54:1 by weight, 1.53:1 by weight, 1.52:1 by weight, 1.51:1 by weight or 1.5:1 by weight.

In some embodiments, the delivery system further comprises water. The ratio of water to the at least one active agent, at least one non-ionic surfactant and at least one polyol may be from about 4:1 to about 1:1 by weight. Typically, the ratio of water to the at least one active agent, at least one non-ionic surfactant and at least one polyol is from about 3.5:1 to about 2:1 by weight. For example, the ratio of water to the at least one active agent, at least one non-ionic surfactant and at least one polyol may be about 3.5:1 by weight, 3.4:1 by weight, 3.3:1 by weight, 3.2:1 by weight, 3.1:1 by weight, 3.0:1 by weight, 2.9:1 by weight, 2.8:1 by weight, 2.7:1 by weight, 2.6:1 by weight, 2.5:1 by weight, 2.4:1 by weight, 2.3:1 by weight, 2.2:1 by weight, 2.1:1 by weight or 2:1 by weight.

The delivery systems comprise at least one non-ionic surfactant. The at least one non-ionic surfactant may include, but is not limited to, one or more of a polyethoxylated castor oil, polyoxyethylene sorbitan monolaurate, polyoxyethylene sorbitan monoleate and tocopheryl polyethylene glycol succinate, however a person skilled in the art will appreciate that other non-ionic surfactants may also be used. The at least one non-ionic surfactant may obtained by reacting castor oil or hydrogenated castor oil with ethylene oxide. In certain embodiments the at least one non-ionic surfactant comprises glycerol polyethylene glycol ricinoleate, fatty acid esters of polyethylene glycol, free polyethylene glycols and ethoxylated glycerol. In other embodiments the at least one non-ionic surfactant comprises glycerol polyethylene glycol hydroxystearate, fatty acid glycerol polyglycol esters, polyethylene glycols and glycerol ethoxylate. In one embodiment the at least one non-ionic surfactant is a polyethoxylated castor oil.

The delivery systems of the invention comprise at least one polyol. The at least one polyol may include, but is not limited to, glycerol or propylene glycol, however a person skilled in the art will appreciate that other polyols may also be used. In one embodiment the at least one polyol is glycerol.

The delivery systems of the invention comprise at least one active agent. The at least one active agent may be fat soluble and/or water soluble. Examples of suitable active agents include, but are not limited to, one or more of a vitamin, a mineral, a hormone, an active pharmaceutical ingredient, an immunosuppressive agent, an antibiotic, a steroid, a proton pump inhibitor (PPI), a selective serotonin reuptake inhibitor (SSRI), and an angiotensin converting enzyme (ACE) inhibitor, an amino acid, a peptide, a fatty acid, an antioxidant, a non antioxidant a plant extract or synthetic version thereof, a nutraceutical and combinations thereof. Those skilled in the art will appreciate that other active agents may also be used.

In some embodiments the active agent is at least one vitamin selected from the group consisting of vitamin A, vitamin B, vitamin C, vitamin D, vitamin E and vitamin K. In particular embodiments the active agent is a combination of vitamins.

In some embodiments the vitamin is vitamin A.

In some embodiments the vitamin is vitamin B selected from the group consisting of vitamin B1, vitamin B2, vitamin B5, vitamin B6, vitamin B7, vitamin B9 and vitamin B12. Those skilled in the art will appreciate that the vitamin B may be present in the form of suitable precursors, derivatives or analogues thereof. In one embodiment the vitamin is B12. Typically the B12 is methylcobalamin and/or cyanocobalamin. Delivery systems comprising vitamin B, in particular vitamin B12 find particular use in the treatment of subjects who are vitamin B deficient as a result of impaired vitamin B uptake as result of a poorly functioning gastrointestinal system and/or resulting from age related issues.

In some embodiments the vitamin is vitamin C.

In some embodiments the vitamin is vitamin D. In particular embodiments the vitamin D is vitamin D2 or vitamin D3. Those skilled in the art will appreciate that the vitamin D may be present in the form of suitable precursors, derivatives or analogues thereof. Typically the vitamin D3 is cholecalciferol. However, a person skilled in the art will appreciate that the vitamin D3 may be in the form of any suitable precursor, derivative or analogue thereof. In some embodiments the delivery system comprises vitamin D2 (ergocalciferol), or metabolites, analogues or derivatives thereof. Delivery systems comprising vitamin D, in particular vitamin D3 find particular use in the treatment of subjects who are vitamin D deficient as a result of impaired vitamin D uptake as result of a poorly functioning gastrointestinal system and/or resulting from age related issues.

In some embodiments the vitamin is vitamin E. Those skilled in the art will appreciate that the vitamin E may be present in the form of suitable precursors, derivatives or analogues thereof. Typically, the vitamin E is d-alpha-tocopherol. In a particular embodiment the active agent is a combination of vitamin E and vitamin B12.

In some embodiments the vitamin is vitamin K. The vitamin K may be vitamin K1 and/or vitamin K2. Those skilled in the art will appreciate that the vitamin K may be present in the form of suitable precursors, derivatives or analogues thereof. Typically the vitamin K is vitamin K2. Typically, the vitamin K2 is menaquinone. The Vitamin K2 may be any subtype. Typically the subtype is menaquinone-4 or menaquinone-7. In a particular embodiment the active agent is a combination of vitamin K2 (menaquinone-4) and vitamin D3. In another particular embodiment the active agent is a combination of vitamin K2 (menaquinone-7) and vitamin D3. In one embodiment the vitamin is a combination of vitamin D3 and vitamin K2. In exemplary embodiments in which the active agent is a combination of vitamin D3 and vitamin K2, the particle size may be about 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, or 40 nm, in particular embodiments the particle size is about 25 nm, 26 nm, 27 nm, 28 nm, 29 nm, or 30 nm.

In some embodiments the at least one active agent is a statin. The statin may be a fat soluble statin or a water soluble statin. Examples of suitable fat soluble statins include, but are not limited to, atorvastatin, cerivastatin, fluvastatin, lovastatin, mevastatin, and simvastatin, and salts and combinations thereof. Suitable salts of, for example atorvastatin for use in accordance with embodiments of the present disclosure include, but are not limited to, atorvastatin calcium, atorvastatin magnesium, and atorvastatin sodium. Those skilled in the art will appreciate that other salts may also be employed and the scope of the present disclosure is not limited by reference to any particular salt. In exemplary embodiments in which the active agent is atorvastatin calcium, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm. Examples of suitable water soluble statins include, but are not limited to, pravastatin, fluvastatin and rosuvastatin, and salts and combinations thereof. Suitable salts of, for example rosuvastatin for use in accordance with embodiments of the present disclosure include, but are not limited to, rosuvastatin calcium, rosuvastatin manganese, and rosuvastatin sodium. Those skilled in the art will appreciate that other salts may also be employed and the scope of the present disclosure is not limited by reference to any particular salt. Those skilled in the art will appreciate that other statins may also be used and the scope of the present disclosure is not limited by reference to any particular statin. In exemplary embodiments in which the active agent is rosuvastatin calcium, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm.

In some embodiments the at least one active agent is an antibiotic. Examples of antibiotics include, but are not limited to, amikacin, gentamicin, kanamycin, neomycin, netilmicin, tobramycin, paromomycin, streptomycin, spectinomycin, gelanamycin, herbimycin, rifaximin, loracarbef, ertapenem, doripenem, imipenem, meropenem, cefadroxil, cefazolin, cefalotin, cephalexin, cefaclor, cefamandole, cefoxitin, cefuroxime, cefixime, cefdinir, cefditoren, cefoperazone, cefotaxime, cefpodozime, ceftazidime, cefepime, ceftaroline, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, azetreonam, furazolidone, nitrofurantoin, linezolid, posizolid, radezolid, torezolid, amoxicillin, ampicillin, azlocillin, carbenicillin, cloxacillin, flucloxacillin, mezlocillin, methicillin, nafcillin, oxacillin, penicillin, piperacillin, temocillin, tiarcillin, bacitracin, colistin, polymyxin, ciprofloxacin, enoxacin, gatifloxacin, gemifloxacin, levofloxacin, ofloxacin, mafenide, sulfacetamide, sulfadiazine, sulfamethoxazole, doxycycline, minocycline, oxytetracycline, tetracycline, clofazimine, arsphenamine, chloramphenicol, and thiamphenicol. Those skilled in the art will appreciate that other antibiotics may also be employed and the scope of the present disclosure is not limited by reference to any particular antibiotic. In exemplary embodiments in which the active agent is ampicillin sodium, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm.

In some embodiments the at least one active agent is a steroid. The steroid may be dexamethasone, however a person skilled in the art will appreciate that other antioxidants may also be used. In exemplary embodiments in which the active agent is dexamethasone, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm.

In some embodiments the at least one active agent is a selective serotonin reuptake inhibitor (SSRI). Examples of SSRIs include, but are not limited to, citalopram, fluvoxamine, escitalopram, paroxetine, sertraline and fluoxetine. Those skilled in the art will appreciate that other SSRIs may also be employed and the scope of the present disclosure is not limited by reference to any particular SSRI. In exemplary embodiments in which the active agent is sertraline hydrochloride, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 13 nm, 14 nm, 15 nm, 16 nm, 17 nm, or 18 nm.

In some embodiments the at least one active agent is an angiotensin converting enzyme (ACE) inhibitor. Examples of ACE inhibitors include, but are not limited to, captopril, zofenopril, enalapril, ramipril, quinapril, perindopril, lisinopril, benzepril, imidapril, trandolapril, cilazapril and fosinopril. Those skilled in the art will appreciate that other ACE inhibitors may also be employed and the scope of the present disclosure is not limited by reference to any particular ACE inhibitor. In exemplary embodiments in which the active agent is perindopril erbumine, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm.

In some embodiments the active agent is an antioxidant. Typically the antioxidant is Coenzyme Q10, however a person skilled in the art will appreciate that other antioxidants may also be used. In exemplary embodiments in which the active agent is Coenzyme Q10, the particle size may be about 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, or 55 nm, in particular embodiments the particle size is about 34 nm, 35 nm, 36 nm, 37 nm, 38 nm, 39 nm, or 40 nm.

In some embodiments the active agent is a plant extract. The plant extract can be a natural extract or a synthetic version thereof. Exemplary extracts may comprise a cannabis extract, one or more cannabinoids, for example a phytocannabinoid such as tetrahydrocannabinol, hemp oil or resveratrol, however a person skilled in the art will appreciate that other extracts may also be used. In a particular embodiment the active agent is a combination of resveratrol and vitamin B12. In a particular embodiment the active agent is hemp oil. In exemplary embodiments in which the active agent is of resveratrol and vitamin B12, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, or 35 nm, in particular embodiments the particle size is about 15 nm, 16 nm, 17 nm, 18 nm, 19 nm, or 20 nm.

In some embodiments the active agent is a mineral selected from the group consisting of zinc, calcium, chromium, cooper, iron, magnesium, manganese, phosphorus, potassium. In a particular embodiment the mineral is zinc. In a particular embodiment the active agent is a combination of zinc, carnosine and a probiotic microorganism. In another particular embodiment the active agent is a combination of zinc, N-acetylcarnosine and a probiotic microorganism.

In some embodiments the active agent is a hormone. The hormone may be selected from the group consisting of melatonin, testosterone, insulin, progesterone and estrogen, however a person skilled in the art will appreciate that other hormones may also be used. In one embodiment the hormone is melatonin. In exemplary embodiments in which the active agent is melatonin, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, or 40 nm, in particular embodiments the particle size is about 20 nm, 21 nm, 22 nm, 23 nm, 24 nm, or 25 nm. In particular embodiments the melatonin may be in combination with a vitamin such as, but not limited to, vitamin B6. Delivery systems comprising melatonin may find particular use for those subjects who have difficulty sleeping, such as subjects with jet lag or insomniacs. In one embodiment the hormone may be testosterone. The testosterone may be testosterone propionate. In exemplary embodiments in which the active agent is testosterone propionate, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 10 nm, 11 nm, 12 nm, 13 nm, 14 nm, or 15 nm. In a particular embodiment the hormone is insulin. Delivery systems comprising insulin may find particular use in the treatment of diabetes; for regulating blood glucose levels and/or for preventing or treating hyperglycaemia particularly in those individuals who are unable to tolerate administration of insulin via the traditional injection methods. In exemplary embodiments in which the active agent is insulin, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 1 nm, 2 nm, 3 nm, 4 nm, or 5 nm. In one embodiment the hormone is progesterone, estrogen or a combination thereof. Delivery systems comprising a progestogen, such as but not limited to progesterone, and/or an estrogen, such as but not limited to beta-estradiol, may find particular use as a female contraceptive or as a hormone replacement. In exemplary embodiments in which the active agent is progesterone, the particle size may be about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 12 nm, 13 nm, 14 nm, 15 nm, 16 nm, 17 nm, or 18 nm. In exemplary embodiments in which the active agent is beta-estradiol, the particle size may be from about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, or 30 nm, in particular embodiments the particle size is about 12 nm, 13 nm, 14 nm, 15 nm, 16 nm, 17 nm, or 18 nm.

In some embodiments the active agent may be a fatty acid, for example docosahexaenoic acid (DHA) and/or arrachidonic acid (AA).

In some embodiments the active agent is selected from the group consisting of orotic acid, L-carnitine, L-carnisine, and a yeast derived extract.

In further embodiments the delivery systems may further comprise at least one flavour. In particular embodiments the flavour is a natural oil. Typically, the natural oil is peppermint oil or orange oil, however a person skilled in the art will appreciate that other natural oils may also be used to impart a pleasant flavour and/or aroma to the delivery systems.

In further embodiments the delivery systems may further comprise at least one acidulant. Typically the at least one acidulant is citric acid, acetic acid or lactic acid, however a person skilled in the art will appreciate that other acidulants may also be used to modify and/or maintain the pH of the delivery systems. In a particular embodiment the acidulate is citric acid.

In further embodiments the delivery systems may further comprise at least one preservative. Typically the at least one preservative is potassium sorbate or phenoxyethanol, however a person skilled in the art will appreciate that other preservatives may also be used.

In further embodiments the delivery system may further comprise at least one sweetener. The at least one sweetener is typically, but not limited to, a natural sweetener. The natural sweetener may be stevia, erythritol, xylitol, mannitol and/or sorbitol, however a person skilled in the art will appreciate that other natural sweeteners may also be used. In particular embodiments the natural sweetener is stevia.

It is contemplated that the delivery systems of the invention may comprise one or more probiotic microorganisms. The one or more probiotic microorganisms may be present in the delivery systems as specially selected strains as a culture concentrate or as part of a multiple strain blend with a variety of excipients. The one or more probiotic microorganisms may include but are not limited to one or more of a strain of *Lactobacillus, Bifidobacterium, Streptococcus Saccharomyces, Bacillus, Enterococcus, Bacteroides* or *Propionibacterium*.

Exemplary probiotic strains include *Lactobacillus rhamnosus, Lactobacillus plantarum, Lactobacillus bulgaricus, Lactobacillus gasseri, Lactobacillus reuteri, Lactobacillus paracasei, Lactobacillus casei, Lactobacillus acidophilus, Lactobacillus fermentum, Lactobacillus salvarius, Lactococcus lactis, Streptococcus thermophilus, Bifidobacterium breve, Bifidobacterium bifidum, Bifidobacterium animalis* subsp. *lactis (B. lactis), Bifidobacterium animalis* subsp. *animalis (B. animalis), Bifidobacterium infantis, Bifidobacterium longum* and *Bifidobacterium pseudocatenulatum.*

In some embodiments the amount of the at least one active agent in the delivery system may be approximately 0.1% to 20% by weight. In other embodiments the amount of the at last one active agent is from 0.5% to 10% by weight. Alternatively, the amount of the at last one active agent in the delivery system may be about 1%, 1.5%, 2%, 2.5%, 3%, 3.5%, 4%, 4.5%, 5%, 5.5%, 6%, 6.5%, 7%, 7.5%, 8%, 8.5%, 9% or 9.5% by weight.

The skilled artisan will appreciate that the delivery systems according to the invention will find use in methods for managing, preventing and/or treating diseases or conditions in accordance with any and all indications to which the active agent of choice finds use. For example, when the active agent is a statin the delivery systems will find use in methods for preventing and/or reducing blood cholesterol, treating dyslipidemia and preventing and/or treating cardiovascular disease. When the active agent is insulin the delivery systems according to the invention will find use in the management of diabetes. The skilled artisan will appreciate that these active agents and others to which delivery systems of the invention relate, are not limited to known treatments.

The skilled addressee will appreciate that the specific dosing regimen (with respect for example to frequency and duration of administration) to be employed in accordance with embodiments of the invention may be determined on a case-by-case basis. Such determinations are well within the capabilities of those skilled in the art without undue burden or experimentation.

Further, it will be understood that the specific dose level of a delivery system of the invention for any particular individual will depend upon a variety of factors including, for example, the activity of the vitamin, mineral or active pharmaceutical ingredient employed, the age, body weight, general health and diet of the individual to be treated, the time of administration, rate of excretion, and combination with any other treatment or therapy. Single or multiple daily administrations can be carried out with dose levels. A broad range of doses may be applicable.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

Example 1—Preparation of Vitamin D3 (Cholecalciferol) Oral Spray Delivery System 23.333 g cholecalciferol (2.233% by weight) in an oil form standardized at 1 million IU/g, was added to 157 g PEG 40 castor oil heated to 70° C. 0.167 g peppermint oil was then added followed by 105 g heated glycerol. An aqueous solution containing 1.9 g of citric acid and 1.067 g of potassium sorbate dissolved in 756 g water was then added. When cooled 0.50 g stevia was added. The resulting clear micelle composition had a specific gravity of 1.045 g/mL and pH of 3.99 with a dose of 5000 IU cholecalciferol per two sprays (0.3 mL). The viscosity measured at 25° C. with a Brookfield viscometer (Spindle #1 at 20 rpm) was 17.5 cP. The particle size determined using a NanoSight LM10-HSBT14 nanoparticle tracking analysis showed a mean particle size of 194 nm and a mode particle size of 166 nm (standard deviation of 57 nm).

Example 2—Vitamin B12 (Methylcobalamin) and Resveratrol Oral Spray Delivery System 7.143 g resveratrol (0.682% by weight) was added to 158 g PEG 40 castor oil heated to 70° C. 0.167 g peppermint oil was then added followed by 107 g heated glycerol. An aqueous solution containing 4.714 g methylcobalamin, 1.67 g citric acid and 1.067 g of potassium sorbate dissolved in 768 g water was then added. When cooled 0.50 g of stevia was added. The resulting clear micelle composition had a specific gravity of 1.048 g/mL and pH of 3.95 with a dose of 1000 μg methylcobalamin and 2 mg resveratrol per two sprays (0.3 mL).

Example 3—Vitamin B12 (Cyanocobalamin) and Vitamin E (d-alpha-tocopherol) Oral Spray Delivery System 5.385 g d-alpha-tocopherol (0.520% by weight) was added to 158 g PEG 40 castor oil heated to 60° C. 0.167 g peppermint oil was then added followed by 107 g heated glycerol An aqueous solution containing 4.714 g cyanocobalamin, 1.67 g citric acid and 1.067 g potassium sorbate dissolved in 757 g water was then added. When cooled, 0.50 g of stevia was added. The resulting clear micelle composition had a specific gravity of 1.035 g/mL and a pH of 3.95 with a dose of 1000 μg cyanocobalamin and 2 IU d-alpha-tocopherol per two sprays (0.3 mL).

Example 4—Melatonin Oral Spray Delivery System 11.224 g melatonin powder (1.090% by weight) was added to 157 g PEG 35 castor oil heated to 70° C. 0.333 g orange oil was then added followed by 105 g heated glycerol. An aqueous solution containing 1.90 g citric acid and 1.067 g potassium sorbate dissolved in 753 g water was then added. When cooled, 0.50 g of stevia was added. The resulting clear micelle composition had a specific gravity of 1.030 g/mL and a pH of 4.00 with a dose of 3 mg melatonin per two sprays (0.3 mL). The particle size determined using a Malvern Zetasizer showed a mean particle size of 22.98 nm (PDI=0.19).

Example 5—Melatonin and 86 Oral Spray Delivery System 9.354 g melatonin powder (0.8677% by weight) and 5.170 g B6 as pyridoxine hydrochloride (0.4796% by weight) was added to 133.3 g medium chain triglycerides and 22.3 g Cremophor RH 40 heated to 70° C. 6.667 g peppermint oil was then added followed by 66.7 g heated glycerol. An aqueous solution containing 1.53 g citric acid and 1.10 g potassium sorbate dissolved in 831 g water was then added. When cooled, 0.50 g of stevia was added. The resulting clear micelle composition had a specific gravity of 1.078 g/mL and a pH of 3.8 with a dose of 2.5 mg melatonin and 1 mg B6 per two sprays (0.3 mL).

Example 6—Vitamin D3 (Cholecalciferol) and Vitamin K2 (Menaquinone) Oral Spray Delivery System 23.333 g cholecalciferol (2.231% by weight) and 0.541 g menaquinone-4 (0.0517%) was added to 157 g PEG 35 castor oil heated to 70° C. 0.167 g peppermint oil was then added followed by 105 g heated glycerol. An aqueous solution containing 2.00 g citric acid and 1.067 g potassium sorbate dissolved in 757 g of water was then added. When cooled, 0.50 g of stevia was added. The resulting clear micelle composition had a specific gravity of 1.046 g/mL and a pH of 3.98 with a dose of 5000 IU of cholecalciferol and 150 µg menaquinone-4 per two sprays (0.3 mL). The particle size determined using a Malvern Zetasizer showed a mean particle size of 28.01 nm (PDI=0.18).

Example 7—Vitamin A and Zinc Oral Spray Delivery System 0.9339 Vitamin A propionate oil (0.8116% by weight) was added to 13.33 g Kolliphor EL heated to 70° C. 0.20 g peppermint oil was then added followed by 10.0 g heated glycerol. An aqueous solution containing 1.084 g zinc gluconate, 0.217 g citric acid and 0.110 g potassium sorbate dissolved in 89.246 g of water was then added. The resulting clear micelle composition had a specific gravity of 1.150 g/mL and a pH of 3.9 with a dose of 5000 IU of Vitamin A and 400 µg zinc per two sprays (0.3 mL).

Example 8—Coenzyme Q10 (Ubiquinone) Oral Spray Delivery System 35.714 g ubiquinone (3.344% by weight) was added to 189 g PEG 35 castor oil heated to 70° C. 0.167 g of peppermint oil was then added followed by 104 g heated glycerol. An aqueous solution containing 1.80 g citric acid and 1.111 g potassium sorbate dissolved in 714 g water was then added. When cooled, 0.50 g of stevia was added. The resulting clear micelle composition had a specific gravity of 1.068 g/mL and a pH of 4.0 with a dose of 30 mg of ubiquinone per six sprays (0.9 mL). The particle size determined using a Malvern Zetasizer showed a mean particle size of 32.30 nm (PDI=0.13).

Example 9—Vitamin D3 (Cholecalciferol) and Vitamin K2 (Menaquinone) Oral Spray Delivery System 4.667 g cholecalciferol (0.4212% by weight) and 30.9 g menaquinone-7 (2.7888% by weight) was added to 193.3 g Cremophor RH 40 heated to 70° C. 0.333 g peppermint oil was then added followed by 93.3 g heated glycerol. An aqueous solution containing 2.267 g citric acid and 1.133 g potassium sorbate dissolved in 782 g of water was then added. When cooled, 0.50 g of stevia was added. The resulting clear micelle composition had a specific gravity of 1.108 g/mL and a pH of 4.00 with a dose of 1000 IU of cholecalciferol and 45 µg menaquinone-7 per two sprays (0.3 mL).

Example 10—Industrial Preparation of Vitamin D3 (Cholecalciferol) Oral Spray Delivery System of Example 1

The vitamin D3 spray of Example 1 was prepared as a large manufacturing scale batch as follows:
1. In a suitable jacketed vessel the Cremophor RH 40 was heated to ~70° C.
2. Vitamin D3 oil was added and stirred until clear.
3. Peppermint oil was added and stirred until clear.
4. Glycerine was added and stirred until homogeneous.
5. In a separate heating vessel water was heated to ~70° C.
6. Citric acid was added to the heated water and completely dissolved.
7. Potassium sorbate was slowly added to the heated water until completely dissolved.
8. The heated water solution was slowly added to the Cremophor RH 40, Vitamin D3, peppermint oil and glycerine mixture. The resulting solution was slightly cloudy.
9. The resulting solution was allowed to cool while stirring. The solution became clear as it approached room temperature.
10. Stevia was added and stirred until dissolved.
11. Additional water was added, if necessary, to ensure a final concentration of 1.045 g/ml.

Example 11—Industrial Preparation of Vitamin B12 (Methylcobalamin) and Resveratrol Oral Spray Delivery System The vitamin B12 and resveratrol spray of Example 2 was prepared as a large manufacturing scale batch as follows:
1. In a suitable jacketed vessel the Cremophor RH 40 was heated to ~70° C.
2. Resveratrol powder was added and stirred until clear.
3. Peppermint oil was added and stirred until clear.
4. Glycerine was added and stirred until homogeneous.
5. In a separate heating vessel water was heated to ~70° C.
6. Citric acid was added to the heated water and completely dissolved.
7. Potassium sorbate was slowly added to the heated water until completely dissolved.
8. The water solution was allowed to cool to about 50° C. and vitamin B12 powder was added.
9. The heated water solution was slowly added to the Cremophor RH 40, resveratrol, peppermint oil and glycerine mixture. The resulting solution was red and slightly cloudy.
10. The resulting solution was allowed to cool while stirring. The solution became clear red as it approached room temperature.
11. Stevia was added and stirred until dissolved.
12. Additional water was added, if necessary, to ensure a final concentration of 1.048 g/ml.

Example 12—Industrial Preparation of Vitamin B12 (Cyanocobalamin) and Vitamin E (d-alpha-tocopherol) Oral Spray Delivery System The vitamin B12 and vitamin E spray of Example 3 was prepared as a large manufacturing scale batch as follows:

1. In a suitable jacketed vessel the Cremophor RH 40 was heated to ~60° C.
2. Vitamin E oil was added and stirred until clear.
3. Peppermint oil was added and stirred until clear.
4. Glycerine was added and stirred until homogeneous.
5. In a separate heating vessel water was heated to ~60° C.
6. Citric acid was added to the heated water and completely dissolved.
7. Potassium sorbate was slowly added to the heated water until completely dissolved.
8. The water solution was allowed to cool to about 50° C. and vitamin B12 powder was added.
9. The heated water solution was slowly added to the Cremophor RH 40, vitamin E, peppermint oil and glycerine mixture. The resulting solution was red and slightly cloudy.
10. The resulting solution was allowed to cool while stirring. The solution became clear red as it approached room temperature.
11. Stevia was added and stirred until dissolved.
12. Additional water was added, if necessary, to ensure a final concentration of 1.035 g/ml.

Example 13—Industrial Preparation Vitamin A with Zinc Oral Spray Delivery System The vitamin A and zinc Oral Spray delivery system (5000 IU Vitamin A and 400 µg zinc per 0.3 mL) of Example 9 was prepared as a large manufacturing scale batch as follows:
1. In a suitable jacketed vessel Kolliphor EL was heated to ~70° C.
2. vitamin a proprionate oil was added and stirred until clear.
3. Peppermint oil was added and stirred until clear.
4. Glycerine was added and stirred until homogeneous.
5. In a separate heating vessel water was heated to ~70° C.
6. Zinc gluconate was added to heated water and stirred until completely dissolved.
7. Citric acid was added to the heated water and stirred until completely dissolved.
8. Potassium sorbate was added to the heated water until completely dissolved.
9. The heated water solution was slowly added to the Kolliphor EL, vitamin A proprionate, peppermint oil and glycerine mixture. The resulting solution was slightly cloudy.
10. The resulting solution was allowed to cool while stirring. The solution became clear as it approached room temperature.
11. Additional water was added, if necessary, to ensure a final concentration of 1.50 g/ml.
12. The pH was ~3.9.

Example 14—Case Study: Administration of Vitamin D3 (cholecalciferol) Oral Spray Delivery System of Example 1

A senior male with borderline vitamin D deficiency for several years (30 ng/mL vitamin D blood level, normal range 30 to 80 ng/mL) was administered with 5000 IU of the Vitamin D3 oral spray of Example 1 per day for 60 days. After 30 days the level of vitamin D in his blood was 44 ng/mL (increase of 46%). After 60 days the level of vitamin D in his was 55 ng/mL (increase of 83% from baseline) showing an return to mid normal range.

Example 15—Preparation of 2 mg/mL Atorvastatin Calcium Spray Delivery System 0.5 mL ethanol and 0.45 g caprylic acid were added to 10 mg atorvastatin calcium and heated to 60° C. until the atorvastatin completely dissolved. 1.5 g (Cremophor RH40 preheated to 60° C. was added to the atorvastatin calcium solution and the resulting mixture was stirred until clear. 0.5 g glycerine was added and the solution stirred until homogeneous. Water preheated to 60° C. was then slowly added to make a final solution of 5 mL. The resulting solution was allowed to cool whilst stirring.

Example 16—Preparation of 2 mg/mL Atorvastatin Calcium Spray Delivery System

250 µL caprylic acid were added to 10 mg atorvastatin calcium and heated to 60° C. until the atorvastatin completely dissolved. 1 g Cremophor RH40 preheated to 60° C. was added to the atorvastatin calcium solution and the resulting mixture was stirred until clear. 0033 g glycerine was added and the solution stirred until homogeneous. Water preheated to 60° C. was then slowly added to make a final solution of 5 mL. The resulting solution was allowed to cool whilst stirring.

Example 17—Preparation of 1.67 mg/mL Atorvastatin Calcium Spray Delivery System 9 g caprylic acid were added to 333 mg atorvastatin calcium and heated to 60° C. until the atorvastatin completely dissolved. 50 g Cremophor RH40 preheated to 60° C. was added to the atorvastatin calcium solution and the resulting mixture was stirred until clear. 16.7 g glycerine was added and the solution stirred until homogeneous. An aqueous solution containing 380 mg citric acid and 214 mg potassium sorbate dissolved in 100 mL of water was then added. The resulting solution was allowed to cool whilst stirring. Additional water was added, if necessary, to ensure a final concentration of 1.67 mg/mL.

Example 18—Preparation of 10 mg/mL Atorvastatin Calcium Spray Delivery System 1.5 mL caprylic acid were added to 500 mg atorvastatin calcium and heated to 60° C. until the atorvastatin completely dissolved. 17.5 g Cremophor RH40 preheated to 60° C. was added to the atorvastatin calcium solution and the resulting mixture was stirred until clear. 6 g glycerine was added and the solution stirred until homogeneous. An aqueous solution containing 380 mg citric acid and 214 mg potassium sorbate dissolved in 100 mL of water was then added. The resulting solution was allowed to cool whilst stirring. Additional water was added, if necessary, to ensure a final concentration of 10 mg/mL.

Example 19—Particle Size Analysis of Atorvastatin Spray Delivery System

The particle size of Atorvastatin Calcium Spray Delivery System prepared by the methods outlined in Examples 16, 17 and 18 was determined using a Malvern Zetasizer (samples diluted 1 in 20 due to viscosity).

TABLE 1

| | Intensity - Weighted | | | | |
|---|---|---|---|---|---|
| | | Cumulant Results | | Non-Negative Least Squares (NNLS) Results | |
| Sample ID | Concentration (mg/mL) | Z-Average (nm) | PDI | Peak 1 (nm) | Peak 1 Width (nm) |
| Atorvastatin 1022015ATO | 2 | 11.41 | 0.03 | 12.04 | 2.996 |
| Atorvastatin-25 12142015ATO25 | 1.67 | 14.62 | 0.04 | 15.49 | 3.933 |
| Atorvastatin-30 12142015ATO30 | 1.67 | 14.37 | 0.08 | 15.66 | 4.625 |
| Atorvastatin 2162016ATO | 10 | 12.71 | 0.10 | 13.99 | 4.563 |

Example 20—Preparation of 5 mg/mL Rosuvastatin Spray Delivery System

250 μL caprylic acid were added to 25 mg rosuvastatin and heated to 60° C. until the rosuvastatin completely dissolved. 1 g Cremophor RH40 preheated to 60° C. was added to the rosuvastatin solution and the resulting mixture was stirred until clear. 0.33 g glycerine was added and the solution stirred until homogeneous. Water preheated to 60° C. was added to the resulting solution to make a total volume of 5 mL. The resulting solution was allowed to cool whilst stirring.

Example 21—Particle Size Analysis of Rosuvastatin Spray Delivery System

The particle size of Rosuvastatin Spray Delivery System of Example 20 was determined using a Malvern Zetasizer.

TABLE 2

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 1022015ROS | 12.19 | 0.03 | 12.82 | 3.148 |

Example 22—Preparation of 5 mg/mL Testosterone Propionate Spray Delivery System 1.5 mL caprylic acid was added to 150 mg testosterone propionate and heated to 60° C. until the testosterone propionate completely dissolved. 10.5 g Cremophor RH40 preheated to 60° C. was added to the testosterone propionate solution and the resulting mixture was stirred until clear. 4.5 g glycerine was added and the solution stirred until homogeneous. Water preheated to 60° C. was added to the resulting solution to make a total volume of 30 mL. The resulting solution was allowed to cool whilst stirring.

Example 23—Particle Size Analysis of Testosterone Propionate Spray Delivery System The particle size of testosterone propionate spray delivery system of Example 22 was determined using a Malvern Zetasizer.

TABLE 3

| Sample ID | Cumulant Results Z-Average (nm) | PDI | Non-Negative Least Squares (NNLS) Results Peak 1 (nm) | Peak 1 Width (nm) |
|---|---|---|---|---|
| | Intensity - Weighted | | | |
| 1232015TES | 14.30 | 0.02 | 15.02 | 3.623 |

Example 24—Preparation of 15 IU/mL Insulin Spray Delivery System

A solution of human insulin with a concentration of 10 mg/mL was prepared by dissolving the insulin in deionsed water and adjusting the pH of the solution to 3 using 0.1 M hydrochloric acid. 1.5 mL. 0.75 g Cremophor RH40 preheated to 40° C. was added to 30 mg d-alpha-tocopherol and the resulting mixture was stirred until clear. 0.5 g glycerine was added to the Cremophor RH40 and d-alpha-tocopherol mixture. The insulin solution was added to the Cremophor RH40, d-alpha-tocopherol and glycerine mixture. The resulting solution was allowed to cool whilst stirring.

Example 25—Particle Size Analysis of Insulin Spray Delivery System

The particle size of the insulin spray delivery system of Example 24 was determined using a Malvern Zetasizer.

TABLE 4

| Sample ID | Cumulant Results Z-Average (nm) | PDI | Non-Negative Least Squares (NNLS) Results Peak 1 (nm) | Peak 1 Width (nm) | Peak 2 (nm) | Peak 2 Width (nm) | Peak 3 (nm) | Peak 3 Width (nm) |
|---|---|---|---|---|---|---|---|---|
| | Intensity-Weighted | | | | | | | |
| 1022015INS | 3.843 | 0.25 | 4.217 | 1.710 | 472.9 | 415.0 | 3596 | 1151 |

Example 26—Particle Size Analysis of Vitamin B12 (methylcobalamin) and Resveratrol Oral Spray Delivery System The particle size of the Vitamin B12 and resveratrol spray delivery system of Example 2 was determined using a Malvern Zetasizer.

TABLE 5

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2182016B12 | 18.89 | 0.18 | 22.65 | 9.861 |

Example 27—Preparation of 7 µg/mL Perindopril Erbumine Spray Delivery System 100 µL caprylic acid was added to 35 mg perindopril erbumine and heated to 60° C. until the perindopril erbumine completely dissolved. 0.75 g Cremophor RH40 preheated to 60° C. was added to the perindopril erbumine solution and the resulting mixture was stirred until clear. 0.25 g glycerine was added and the solution stirred until homogeneous. Water preheated to 60° C. was added to the resulting solution to make a total volume of 5 mL. The resulting solution was allowed to cool whilst stirring.

Example 28—Particle Size Analysis of Perindopril Erbumine Oral Spray Delivery System The particle size of perindopril erbumine spray delivery system of Example 27 was determined using a Malvern Zetasizer.

TABLE 6

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016PER | 12.70 | 0.13 | 14.57 | 5.836 |

Example 29—Preparation of 0.5 mg/mL Sertraline Hydrochloride Spray Delivery System 50 µL dimethyl sulfoxide (DMSO) was added to 2.5 mg sertraline hydrochloride and heated to 60° C. until the sertraline hydrochloride completely dissolved. 0.75 g Cremophor RH40 preheated to 60° C. was added to the sertraline hydrochloride solution and the resulting mixture was stirred until clear. 0.25 g glycerine was added and the solution stirred until homogeneous. Water preheated to 60° C. was added to the resulting solution to make a total volume of 5 mL. The resulting solution was allowed to cool whilst stirring.

Example 30—Particle Size Analysis of Sertraline Hydrochloride Oral Spray Delivery System The particle size of sertraline hydrochloride spray delivery system of Example 29 was determined using a Malvern Zetasizer.

TABLE 7

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016SER | 15.21 | 0.20 | 18.70 | 9.061 |

Example 31—Preparation of 2.6 mg/mL Dexamethasone Spray Delivery System

100 µL caprylic acid was added to 13 mg dexamethasone and heated to 60° C. until the sertraline hydrochloride completely dissolved. 1.5 g Cremophor RH40 preheated to 60° C. was added to the sertraline hydrochloride solution and the resulting mixture was stirred until clear. 0.3 g glycerine was added and the solution stirred until homogeneous. Water preheated to 60° C. was added to the resulting solution to make a total volume of 5 mL. The resulting solution was allowed to cool whilst stirring.

Example 32—Particle Size Analysis of Dexamethasone Oral Spray Delivery System The particle size of the dexamethasone spray delivery system of Example 31 was determined using a Malvern Zetasizer.

TABLE 8

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016DEX | 13.17 | 0.08 | 14.42 | 4.407 |

Example 33—Preparation of 2.6 mg/mL Progestogen Spray Delivery System

500 µL caprylic acid was added to 100 mg progestogen and heated to 60° C. until the progestogen completely dissolved. 15 g Cremophor RH40 preheated to 60° C. was added to the progestogen solution and the resulting mixture was stirred until clear. 5 g glycerine was added and the solution stirred until homogeneous. Water preheated to 60° C. was added to the resulting solution to make a total volume of 50 mL. The resulting solution was allowed to cool whilst stirring.

Example 34—Particle Size Analysis of Progestogen Oral Spray Delivery System

The particle size of the progestogen spray delivery system of Example 33 was determined using a Malvern Zetasizer.

TABLE 9

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016PRO | 15.48 | 0.18 | 17.98 | 7.931 |

Example 35—Preparation of 1 mg/mL Beta-Estradiol Spray Delivery System

500 μL caprylic acid was added to 50 mg beta-estradiol and heated to 60° C. until the beta-estradiol completely dissolved. 15 g Cremophor RH40 preheated to 60° C. was added to the beta-estradiol solution and the resulting mixture was stirred until clear. 5 g glycerine was added and the solution stirred until homogeneous. Water preheated to 60° C. was added to the resulting solution to make a total volume of 50 mL. The resulting solution was allowed to cool whilst stirring.

Example 36—Particle Size Analysis of Beta-Estradiol Oral Spray Delivery System The particle size of the beta-estradiol spray delivery system of Example 35 was determined using a Malvern Zetasizer.

TABLE 10

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016EST | 16.43 | 0.20 | 19.90 | 10.40 |

Example 37—Preparation of 2 mg/mL Ampicillin Sodium Spray Delivery System 100 mg ampicillin was dissolved in 2 mL of deionised water at room temperature. 7.5 g Cremophor RH40 was preheated to 60° C. 500 μL caprylic acid and 2.5 g glycerine was added to the the Cremophor RH40 solution and stirred until homogeneous. The ampicillin solution was added to the solution of Cremophor RH40, caprylic acid and glycerine. Water preheated to 50° C. was added to the resulting solution to make a total volume of 50 mL. The resulting solution was allowed to cool whilst stirring.

Example 38—Particle Size Analysis of Ampicillin Sodium Oral Spray Delivery System The particle size of the ampicillin spray delivery system of Example 37 was determined using a Malvern Zetasizer.

TABLE 11

| | Intensity - Weighted | | | |
|---|---|---|---|---|
| | Cumulant Results | | Non-Negative Least Squares (NNLS) Results | |
| Sample ID | Z-Average (nm) | PDI | Peak 1 (nm) | Peak 1 Width (nm) |
| 2162016AMP | 12.85 | 0.09 | 14.15 | 4.551 |

Example 39—Hemp Seed Oil Transdermal Spray Delivery System 10.35 mg hemp seed oil (3.0026% by weight) was added to 77.00 mg Kolliphor (EL) heated to 70° C. 32.00 mg heated glycerol was added. An aqueous solution containing 0.40 mg citric acid, 2.44 mg phenoxyethanol and 1.75 mg allantoin dissolved in 73.587 g water was then added. The resulting clear micelle composition had a specific gravity of 1.149 g/mL and a pH of about 5.5.

Example 40—Industrial Preparation of 3% Hemp Seed Oil Transdermal Spray Delivery System The hemp seed oil transdermal spray of Example 39 was prepared as a large manufacturing scale batch as follows:
1. In a suitable jacketed vessel Kolliphor EL was heated to ~70° C.
2. Hemp seed oil was added and stirred until clear.
3. Glycerine heated to ~70° C. was added and stirred until homogeneous.
4. In a separate heating vessel water was heated to ~70° C.
5. Phenoxyethanol was added to the heated water and stirred until completely dissolved.
6. Allantoin was added to the heated water and stirred until completely dissolved.
7. Citric acid was added to the heated water and stirred until completely dissolved.
8. The heated water solution was slowly added to the Kolliphor EL, hemp seed oil and glycerine mixture. The resulting solution was slightly cloudy.
9. The resulting solution was allowed to cool while stirring. The solution became clear as it approached room temperature.
10. The resulting pH was ~5.5.

Example 41—1% Vitamin A and Zinc Transdermal Spray Delivery System 1.120 g vitamin A proprionate (0.9614% by weight) was added to 42.00 mg Kolliphor (EL) heated to 70° C. 32500 mg heated glycerol was added. An aqueous solution containing 0.43 mg zinc, 0.40 mg citric acid, 2.45 mg phenoxyethanol, and 1.75 mg allantoin dissolved in 74.691 g water was then added. The resulting clear micelle composition had a specific gravity of 1.165 g/mL and a pH of about 5.5.

Example 42—Industrial Preparation of Vitamin A and Zinc Transdermal Spray Delivery System The vitamin A and zinc transdermal spray of Example 41 was prepared as a large manufacturing scale batch as follows:

1. In a suitable jacketed vessel Kolliphor EL was heated to ~70° C.
2. Vitamin A proprionate oil was added and stirred until clear.
3. Glycerine heated to ~70° C. was added and stirred until homogeneous.
4. In a separate heating vessel water was heated to ~70° C.
5. Zinc gluconate was added to the heated water and stirred until completely dissolved.
6. Phenoxyethanol was added to the heated water and stirred until completely dissolved.
7. Allantoin was added to the heated water and stirred until completely dissolved.
8. Citric acid was added to the heated water and stirred until completely dissolved.
9. The heated water solution was slowly added to the Kolliphor EL, vitamin A proprionate and glycerine mixture. The resulting solution was slightly cloudy.
10. The resulting solution was allowed to cool while stirring. The solution became clear as it approached room temperature.
11. Additional water was added if necessary to the required final concentration od 1.165 g/mL vitamin A.
11. The resulting pH was ~5.5.

The invention claimed is:

1. A transmucosal and/or transdermal delivery system, comprising a micelle composition which comprises:
   one or more surfactants, wherein the one or more surfactants consist of at least one non-ionic surfactant having a Hydrophile-Lipophile Balance (HLB) value of from about 12 to about 16;
   at least one polyol;
   at least one active agent;
   at least one oil; and
   water, at a ratio of said water to the at least one active agent, the at least one non-ionic surfactant and the at least one polyol that is from 4:1 to 1:1 by weight,
   and wherein the micelle composition has: (i) a viscosity of from about 5 cP to about 35 cP when measured at 25° C. on a Brookfield viscometer with spindle #1 at 20 rpm; and (ii) an average particle size of from about 5 nm to about 200 nm.

2. The delivery system of claim 1, wherein the delivery system is delivered via the oral mucosa.

3. The delivery system of claim 1, wherein the at least one oil is medium chain triglycerides, ethyl oleate, ethyl linoleate, caproic acid, caprylic acid, capric acid, or lauric acid, or a combination thereof, or is a natural oil or is derived from a natural oil.

4. The delivery system of claim 3, wherein the natural oil is coconut oil, palm kernel oil, palm oil, lemon oil, sesame oil, vegetable oil, olive oil or sunflower oil, or a combination thereof.

5. The delivery system of claim 1, wherein the at least one non-ionic surfactant is selected from the group consisting of a polyethoxylated castor oil, polyoxyethylene sorbitan monolaurate, polyoxyethylene sorbitan monoleate, tocopheryl polyethylene glycol succinate and mixtures thereof.

6. The delivery system of claim 1, wherein the at least one non-ionic surfactant is obtained by reacting castor oil or hydrogenated castor oil with ethylene oxide.

7. The delivery system of claim 1, wherein the at least one non-ionic surfactant comprises one or more of glycerol polyethylene glycol ricinoleate, fatty acid esters of polyethylene glycol, free polyethylene glycols, ethoxylated glycerol, glycerol polyethylene glycol hydroxystearate, fatty acid glycerol polyglycol esters, polyethylene glycols and glycerol ethoxylate.

8. The delivery system of claim 1, wherein the at least one polyol is selected from the group consisting of glycerol and propylene glycol.

9. The delivery system of claim 1, wherein the micelle composition further comprises a non-aqueous solvent or a mixture of a non-aqueous solvent and water.

10. The delivery system of claim 1, wherein the at least one active agent is provided in an alcohol and oil solution.

11. The delivery system of claim 1, wherein the at least one active agent is selected from a vitamin, a mineral, a hormone, an amino acid, a peptide, a fatty acid, an antioxidant, a plant extract, a nutraceutical, a statin, an immunosuppressive agent, an antibiotic, a sedative, a steroid, a proton pump inhibitor (PPI), a selective serotonin reuptake inhibitor (SSRI), an angiotensin converting enzyme (ACE) inhibitor and combinations thereof.

12. The delivery system of claim 1, wherein the micelle composition further comprises one or more of at least one flavour, at least one acidulant, at least one preservative, and at least one sweetener.

13. The delivery system of claim 12, wherein one or more of: the at least one acidulant is citric acid, the at least one preservative is potassium sorbate or phenoxyethanol, and the at least one sweetener is *stevia*.

14. The delivery system of claim 1, wherein either one or both of (i) a ratio of the at least one active agent to the at least one non-ionic surfactant is from about 1:5 to about 1:15 by weight; and (ii) a ratio of the at least one non-ionic surfactant to the at least one polyol is from about 2:1 to about 1.5:1 by weight.

15. The delivery system of claim 1, wherein the at least one active agent is selected from vitamin A, vitamin B, vitamin C, vitamin D, vitamin E, vitamin K, zinc, calcium, chromium, copper, iron, magnesium, manganese, phosphorus, potassium, melatonin, testosterone, insulin, progesterone, estrogen, Coenzyme Q10, a plant extract comprising resveratrol, a *cannabis* extract, one or more cannabinoids, hemp seed oil, a fat soluble statin and a water soluble statin.

16. The delivery system of claim 1, wherein the delivery system is delivered via the nasal mucosa.

17. The delivery system of claim 1, wherein the delivery system is delivered sublingually or buccally.

18. A method for reducing blood cholesterol or for preventing and/or treating cardiovascular disease or dyslipidemia in a subject, the method comprising administering an effective amount of the delivery system of claim 1 to the subject, wherein the active agent in the delivery system is a statin.

19. A method for treating diabetes, for regulating blood glucose levels and/or for preventing or treating hyperglycemia in a subject, the method comprising administering an effective amount of the delivery system of claim 1 to the subject, wherein the active agent in the delivery system is insulin.

* * * * *